United States Patent [19]

Closse et al.

[11] 4,013,690
[45] Mar. 22, 1977

[54] ORGANIC COMPOUNDS
[75] Inventors: Annemarie Closse, Binningen; Walter Haefliger, Basel; Daniel Hauser, Binningen, all of Switzerland
[73] Assignee: Sandoz Ltd., Basel, Switzerland
[22] Filed: Jan. 30, 1975
[21] Appl. No.: 545,331
[30] Foreign Application Priority Data
    Feb. 5, 1974    Switzerland .................. 1552/74
[52] U.S. Cl. .................. 260/343.3 R; 204/158 R; 260/247.1 T; 260/520 C; 260/520 R; 260/521 R; 260/592; 424/279
[51] Int. Cl.² ........................ C07D 307/86
[58] Field of Search ................ 260/343.3 R
[56] References Cited
UNITED STATES PATENTS
3,829,446   8/1974   Kadin ........................ 260/343.3
FOREIGN PATENTS OR APPLICATIONS
1,014,962   10/1957   Germany ........................ 260/343.3
OTHER PUBLICATIONS
Shibata et al., Chem. Pharm. Bull., 10, 477 (1962).

Beilstein, XVIII, p. 164, 3rd revision.
Spetz, Acta Chem. Scand., 10, 1422 (1956).
Kelly et al., Aust. J. Chem., 22, 977 (1969).

Primary Examiner—Robert Gerstl
Attorney, Agent, or Firm—Gerald D. Sharkin; Robert S. Honor; Thomas O. McGovern

[57] ABSTRACT

This invention provides compounds of formula I,

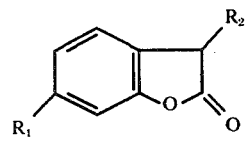

wherein
  $R_1$ is alkyl of 1 to 10 carbon atoms, cycloalkyl of 3 to 8 carbon atoms or phenyl, and
  $R_2$ is hydrogen or alkyl of 1 to 4 carbon atoms,
useful as anti-phlogistics, anti-pyretics, analagesics and inhibitors of blood platelet aggregation.

9 Claims, No Drawings

ORGANIC COMPOUNDS

The present invention relates to new carbocyclic compounds.

In accordance with the invention there are provided new compounds of formula I,

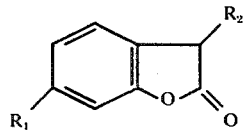

wherein
R₁ is alkyl of 1 to 10 carbon atoms, cycloalkyl of 3 to 8 carbon atoms or phenyl, and
R₂ is hydrogen or alkyl of 1 to 4 carbon atoms, with the proviso that when
R₂ is hydrogen, R₁ is other than methyl.

Further, in accordance with the invention a compound of formula I wherein R₁ and R₂ are as defined above, may be obtained by a process comprising lactonizing a compound of formula II,

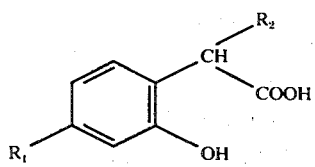

wherein R₁ and R₂ are as defined above.

In the case of R₁, preferred alkyl radicals have from 1 to 4 carbon atoms, especially 2, 3 or 4 carbon atoms. Preferred examples are branched at the a carbon atom, e.g. iso-propyl and isobutyl. Preferred cycloalkyl radicals have from 5 to 7 carbon atoms in the ring thereof, e.g. cyclopentyl and cycloheptyl.

In the case of R₂, preferred alkyl radicals have from 1 to 2 carbon atoms, e.g. methyl.

The reaction may be effected in conventional manner for such lactonization reactions. The reaction may be effected in the presence of an acid. A protonic acid, preferably present in a catalytic amount, may be used, e.g. concentrated sulphuric acid, hydrogen chloride, hydrogen bromide or p-toluene sulphonic acid. Alternatively, a Lewis acid such as a boron trihalide, preferably boron trihalide, preferably boron tribromide may be used.

When a water-binding acid such as hydrogen chloride, concentrated sulphuric acid, or boron tribromide, the reaction may be effected in an inert solvent, at a temperature below reflux temperature. Alternatively, water formed during the lactonization reaction may be continuously removed by co-distillation with a suitable inert solvent, e.g. a suitable aromatic hydrocarbon such as toluene, benzene or xylene.

Compounds of formula II may be produced, for example, by:

a.' splitting the ether group to form a hydroxy group in a compound of formula III

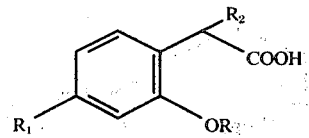

wherein R₁ and R₂ are as defined above, and OR is an ether group capable of being split to form a hydroxy group, or b.' irradiating a compound of formula IV,

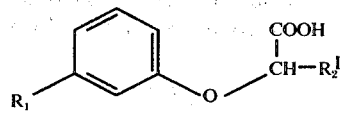

wherein R₁ is as defined above, and R₂' is alkyl with ultra-violet light, to produce a compound of formula II a,

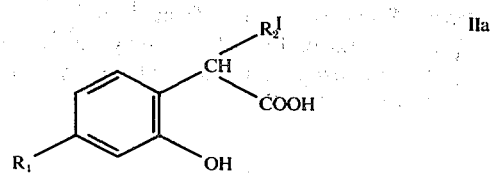

wherein R₁ and R₂' are as defined above.

Process variant (a') is conveniently effected in conventional manner for an ether splitting. Preferably R is methyl. The reaction is preferably effected in the presence of a boron trihalide, especially boron tribromide or with a hydrogen halide such as hydrogen chloride or hydrogen bromide. A suitable inert solvent is methylene chloride, especially when boron tribromide is used. A suitable temperature is from −20 to + 50° C, preferably about 0° C.

R₂ in formula III is preferably hydrogen.

It will be appreciated that the same reaction conditions used for the ether splitting process may be used for the above-indicated lactonization process.

The present invention also provides a process for the production of compounds of formula I as defined above comprising splitting the ether group to form a hydroxy group in a compound of formula III as defined above and lactonizing the resulting compound of formula II as defined above in situ. Preferred reagents for the in situ process include hydrogen bromide, hydrogen chloride or a boron trihalide such as boron tribromide.

Process variant (b') is conveniently effected in conventional manner for a conversion of such phenyl alkyl ethers into 2-alkylphenols under irradiation. For example, ethanol may be used as inert solvent. Argon may be used to provide an inert gas atmosphere.

Compounds of formula III wherein R₂ is hydrogen used as starting materials in process variant (a') may be produced by saponifying a compound of formula V

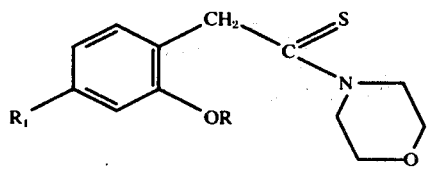

wherein R and $R_1$ are as defined above.

Conventional saponification conditions may be used, e.g. an alcoholic alkali hydroxide solution.

A compound of formula V may be produced for example in conventional manner by reacting sulphur and morpholine with a compound of formula VI

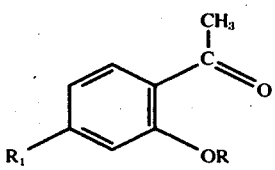

wherein R and $R_1$ are as defined above.

A compound of formula VI may be produced for example in conventional manner by acetylating a compound of formula VII

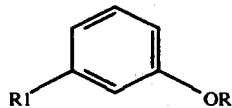

wherein R and $R_1$ are as defined above under Friedel Crafts conditions.

Acetyl chloride is preferably used. As Friedel Crafts catalyst there may be used tin (IV) chloride. An inert solvent such as benzene or carbon tetrachloride may be used. Suitable temperatures are between 0°, e.g. 20 and 80° C.

A compound of formula VII may be produced, for example, by etherifying the corresponding phenol in conventional manner.

Compounds of formula IV, used as starting materials in process variant (b'), may be produced for example by saponifying in conventional manner a compound of formula VIII

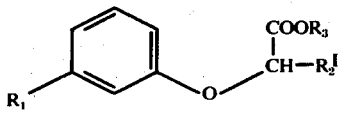

wherein
$R_1$ and $R_2'$ are as defined above, and
$R_3$ is a saponifiable radical.

$R_3$ is preferably alkyl of 1 to 4 carbon atoms. Alcoholic alkali hydroxide solution is preferably used as saponifying agent.

Compounds of formula VIII may be produced, for example, by a conventional Williamson ether synthesis in the presence of a base, e.g. using a compound of formula IX

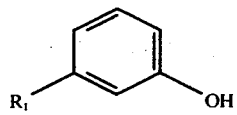

wherein $R_1$ is as defined above, and a compound of formula X

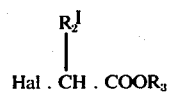

wherein $R_2'$ and $R_3$ are as defined above and Hal is a reactive halogen.

Insofar as the production of any starting material is not particularly described, these compounds are known, or may be produced and purified in accordance with known processes, or in a manner analogue to processes described herein or to known processes.

Free forms of the compounds of formula II may be converted into salt forms in conventional manner and vice versa. A suitable salt form is the sodium salt.

In the following non-limitative Examples all temperatures are indicated in degrees Centigrade. Process variant (a') is used for the preparation of starting materials of formula II in Examples 1–5. Process variant (b') is used in Example 6.

EXAMPLE 1:

6-cyclohexyl-2,3-dihydro-benzofuran-2-one 5.0 g of 4'-cyclohexyl-2'-hydroxy-phenylacetic acid are boiled at reflux in a water separator for two hours in the presence of 50 mg of p-toluenesulphonic acid in 200 cc of toluene. The solution is concentrated by evaporation and the residue is chromatographed on 250 g of silica gel. Elution with methylene chloride yields uniform 6-cyclohexyl-2,3-dihydro-benzofuran-2-one, having a M.P. of 80°–81° after recrystallizing twice from petroleum ether.

The 4'-cyclohexyl-2'-hydroxy-phenylacetic acid, used as starting material, is produced as follows:

a. 4'-cyclohexyl-2'-methoxy-acetophenone 20 g of 3-cyclohexyl anisole are dissolved in 200 cc of benzene, 8.15 g of acetyl chloride are added, and 27.4 g of tin(IV) chloride are subsequently added dropwise at 5°–10° while stirring. After stirring at 23° for 16 hours, the reaction mixture is poured on ice and extracted thrice with benzene. The organic phase is successively washed with 2 N hydrochloric acid, a 2 N caustic soda solution and water, is dried over anhydrous sodium sulphate and concentrated. The residue is recrystallized from acetone/petroleum ether. The resulting title compound has a M.P. of 99°–100°.

b. 4'-cyclohexyl-2'-methoxy-phenylthionoacetic acid morpholide 15.0 g of 4'-cyclohexyl-2'methoxy-acetophenone, 4.05 g of sulphur and 11.0 g of morpholine are boiled at reflux for 16 hours. The reaction mixture is poured on ice and extracted thrice with methylene chloride. The organic phases are washed twice with water, dried over anhydrous sodium sulphate and concentrated. The residue, mainly consisting of 4'-cyclohexyl-2'-methoxy-phenylthionoacetic acid morpholide, is recrystallized from ethanol. M.P. 140°–141°.

c. 4'-cyclohexyl-2'-methoxy-phenylacetic acid 15.0 g of 4'-cyclohexyl-2'-methoxy-phenylthionacetic acid morpholide are suspended in 70 cc of a 3 N caustic potash solution in ethanol and boiling at reflux is effected for 16 hours. The reaction solution is concentrated to a great extent by evaporation, is acidified with 2 N hydrochloric acid and extracted thrice with methylene chloride. The organic phases are washed twice with water, dried over anhydrous sodium sulphate and concentrated. The residue is crystallized from methylene chloride/petroleum ether. The title compound, having a M.P. of 132°–136°, is obtained.

d. 4'-cyclohexyl-2'-hydroxy-phenylacetic acid 6.0 g of 4'-cyclohexyl-2'-methoxy-phenylacetic acid are dissolved in 100 cc of dry methylene chloride, and 12 cc of boron tribromide are added dropwise at 0° while stirring. After 30 minutes, the reaction mixture is added dropwise to approx. 200 cc of a 2 N caustic soda solution while stirring and cooling. The reaction mixture is then acidified to pH 1 with 2 N hydrochloric acid and extracted thrice with methylene chloride. The organic phases are washed twice with water, combined, dried over sodium sulphate and concentrated. The residue is crystallized from methylene chloride/petroleum ether. The resulting 4'-cyclohexyl-2'-hydroxy-phenylacetic acid has a M.P. of 108°–109°.

EXAMPLE 2:

6-cyclopentyl-2,3-dihydro-benzofuran-2-one 5.0 g of 4'-cyclopentyl-2'-hydroxy-phenylacetic acid are heated at reflux in a water separator for 2 hours in the presence of 50 mg of p-toluenesulphonic acid in 200 cc of toluene. The solution is concentrated by evaporation and the residue is chromatographed on 250 g of silica gel. Elution with methylene chloride yields uniform 6-cyclopentyl-2,3-dihydro-benzofuran-2-one, having a M.P. of 42°–43° after recrystallizing twice from petroleum ether.

The 4'-cyclopentyl-2'-hydroxyphenylacetic acid, used as starting material, is produced in a manner analogous to that described in Example 1 (a), (b), (c) and (d).

EXAMPLE 3:

6-cyclohexyl-2,3-dihydro-benzofuran-2-one 4.5 g of 4'-cyclohexyl-2'-methoxy-phenylacetic acid are dissolved in 100 cc of dry methylene chloride, and 10 cc of boron tribromide are added dropwise at 0° while stirring. After 30 minutes, the reaction mixture is added dropwise to 500 cc of ice water while stirring and cooling, and is subsequently extracted thrice with methylene chloride. The ogranic phases are washed twice with water, combined, dried over anhydrous sodium sulphate and concentrated. The crude product is boiled in a water separator together with 20 mg. of p-toluenesulphonic acid in 150 cc of toluene for two hours. The solution is concentrated by evaporation and the residue is chromatographed on 200 g of silica gel. Elution with methylene chloride yields uniform 6-cyclohexyl-2,3-dihydrobenzofuran-2-one, having a M.P. of 80°–81° after crystallizing twice from petroleum ether.

EXAMPLE 4:

2,3-dihydro-6-isobutyl-benzofuran-2-one 7.2 g of 2'-hydroxy-4'-isobutyl-phenylacetic acid are taken up in 100 cc of toluene, 20 mg of p-toluenesulphonic acid are added and the mixture is boiled in a water separator for two hours. The solution is concentrated by evaporation and the residue is chromatographed on 350 g of silica gel. Uniform 2,3-dihydro-6-isobutyl-benzofuran-2-one is isolated with chloroform and has a M.P. of 24°–25° after crystallization from petroleum ether.

The 2'-hydroxy-4'-isobutyl-phenylacetic acid, used as starting material, is produced as follows:

a. 4'-isobutyl-2'-methoxy-acetophenone 46 g of 3-isobutyl anisole are added to 500 cc of absolute benzene, and 22 g of acetyl chloride are added. 73 g of tin(IV) chloride are subsequently added dropwise while stirring and cooling at 5°–10°. After stirring at 23° for 16 hours, the reaction mixture is poured on ice, washed once with 2 N hydrochloric acid, twice with a 2 N caustic soda solution and once with water, and the water phases are again extracted twice with benzene. The organic phases are dried over anhydrous sodium sulphate and concentrated. The desired product is obtained in amorphous, pure form from methanol with the careful addition of water. NMR spectrum (CDCl$_3$) inter alia $\delta$=0.9 d (J=6 Hz), 1.3–2.3 m, 2.45 s, 2.55 s, 3.9 s, 6.6–6.9 m, 7.65 d (J=8.6).

b. 4'-isobutyl-2'-methoxy-phenylthionoacetic acid morpholide 29.1 g of 4'-isobutyl-2'-methoxy-acetophenone, 9.02 g of sulphur and 24.6 g of morpholine are boiled at reflux for 16 hours. The reaction mixture is poured on ice and extracted thrice with methylene chloride, the organic phases are washed with water until the water phase is neutral, drying over anhydrous sodium sulphate and concentration by evaporation are effected. The oily residue is chromatographed on silica gel. The desired compound is eluted with chloroform and is crystallized from ether/petroleum ether. M.P. 81°–83°.

c. 4'-isobutyl-2'-methoxy-phenylacetic acid 22.8 g of 4'-isobutyl-2'-methoxy-phenylthionoacetic acid morpholide are boiled at reflux in 200 cc of a 3 N caustic potash solution in ethanol for two hours, acidification is subsequently effected with 2 N hydrochloric acid, the reaction mixture is diluted with water and extracted with methylene chloride. The methylene chloride phase is washed 4 times with water, dried over sodium sulphate and concentrated by evaporation. The residue can be crystallized from ether/petroleum ether. M.P. 71°–73°.

d. 2'-hydroxy-4'-isobutyl-phenylacetic acid 8 g of 4'-isobutyl-2'-methoxy-phenylacetic acid are dissolved in 20 cc of dry methylene chloride, and 15 cc of boron tribromide are added dropwise at 0° while stirring. The cooling bath is then removed and stirring is continued at room temperature for 30 minutes. The reaction mixture is subsequently added dropwise to approx. 50 cc of a 2 N caustic soda solution while stirring and cooling. The reaction mixture is subsequently acidified to pH 1 with 2 N hydrochloric acid and extracted thrice with methylene chloride. The organic phases are washed twice with water, are combined, dried over sodium sulphate and concentrated by evaporation. The residue is crystallized from petroleum ether. M.P. 81°–82°.

EXAMPLE 5:

2,3-dihydro-6-phenyl-benzofuran-2-one 5g of 2'-hydroxy-4'-phenyl-phenylacetic acid are boiled at reflux in a water separator for two hours in the presence of 50 mg of p-toluenesulphonic acid in 200 cc of toluene. The solution is concentrated by evaporation and the residue is chromatographed on 125 g of silica gel. Elution with methylene chloride yields uniform 2,3-dihydro-6-phenyl-benzofuran-2-one, which after decolouration with active charcoal in methylene chloride, is crystallized from methylene chloride/petroleum ether. M.P. 109°–110°.

NMR spectrum (CDCl$_3$): δ=3.77 S (2H); 7.2–7.7 M (8H).

The 2'-hydroxy-4'-phenyl-phenylacetic acid, used as starting material, is produced as follows:

a. 3-methoxy biphenyl 102 g of 3-hydroxy biphenyl are dissolved in a solution of 67.8 g of potassium hydroxide in 650 cc of water. 86.6 cc of dimethyl sulphate are added dropwise within 30 minutes while stirring, whereby the reaction mixture warms itself. The reaction mixture is then kept at 75° for a further 15 minutes. After 1 hour a further 33.6 g of potassium hydroxide in 45 cc of water are added dropwise, and subsequently 37.8 go of dimethyl sulphate are added dropwise at 65° within 15 minutes. The mixture is again kept at 75° for 1 hour. After cooling, the oily layer is separated and taken up in methylene chloride. Washing is effected once with 2 N sodium hydroxide and once with water. Extraction is again effected twice with methylene chloride. The organic phases are combined, dried over anhydrous sodium sulphate and concentrated. 3-methoxy biphenyl is obtained and is used for the next reaction step without purification.

b. 2'-methoxy-4'-phenyl-acetophenone 52 g of SnCl$_4$ are added dropwise at 5°, while stirring vigorously, to a solution of 36.8 g of 3-methoxy biphenyl and 15.6 g of acetyl chloride in 700 cc of benzene. The mixture is stirred over night at 23°. The reaction mixture is washed twice with 2 N sodium hydroxide and twice with water. Extraction is again effected twice with toluene. The organic phases are combined, dried over anhydrous sodium sulphate and concentrated. 44 g of a crude product are obtained, which are chromatographed on a 20-fold quantity of silica gel. Solvent for absorption and elution: methylene chloride. The crude fractions are crystallized from ether/petroleum ether, whereby 4-acetyl-3-methoxy biphenyl, having an M.P. of 74°–75°, is obtained.

c. 2'-methoxy-4'-phenyl-phenylthionoacetic acid morpholide 17.4 g of 4-acetyl-3-methoxy biphenyl, 14 g of morpholine and 5.1 g of sulphur are heated at reflux for 6 hours. The reaction mixture is taken up in ether, washed once with 2 N hydrochloric acid and twice with water, and is then again extracted twice with ether. The organic phases are combined, dried over anhydrous sodium sulphate and concentrated. Crystallization of the residue from methylene chloride/ether yields 2'-methoxy-4'-phenyl-phenylthionoacetic acid morpholide. M.P. 132°–133°.

d. 2'-methoxy-4'-phenyl-phenylacetic acid 18.8 g. of 2'-methoxy-4'-phenyl-phenylthionoacetic acid morpholide are heated at reflux over night in 90 cc of 3 N potassium hydroxide in ethanol. The reaction mixture is concentrated by evaporation and the residue is dissolved in water, whereby the solution should be strongly alkaline. Extraction is then effected thrice with methylene chloride. The organic phases are washed once with water. The aqueous phases are combined and acidified. Extraction is then effected thrice with ethyl acetate and washing is effected once with water. The ethyl acetate phases are combined, dried over anhydrous sodium sulphate and concentrated. Crystallization of the residue from methylene chloride/petroleum ether yields 2'-methoxy-4'-phenyl-phenylacetic acid. M.P. 164l°–165°.

e. 2'-hydroxy-4'-phenyl-phenylacetic acid 2 g of 2-methoxy-4'-phenyl-phenylacetic acid are dissolved in 60 cc of dry methylene chloride, and 4 cc of boron tribromide are added dropwise at 0°. After 30 minutes at room temperature the mixture is poured on 150 cc of 2 N sodium hydroxide. The mixture is then acidified to pH = 1 with 2 N hydrochloric acid and is extracted thrice with ethyl acetate. The organic phases are washed twice with water, combined, dried over anhydrous sodium sulphate and concentrated. The residue is crystallized from acetone/hexane. The resulting 2'-hydroxy-4'-phenyl-phenylacetic acid has an M.P. of 150°–151°.

Nuclear magnetic resonance spectrum (d$_6$-dimethyl sulphoxide): inter alia δ=3.49 S (2H); 6.9–7.7 (M, 8H).

EXAMPLE 6:

6-cyclohexyl-2,3-dihydro-3-methylbenzofuran-2-one 5g of 2-(4-cyclohexyl-2-hydroxyphenyl)- propionic acid are heated at reflux in a water separator for 2 hours in the presence of 50 mg of p-toluenesulphonic acid in 200 cc of toluene. The solution is concentrated by evaporation and the residue is chromatographed on 500 g of silica gel. Elution with methylene chloride yields pure 6-cyclohexyl-2,3-dihydro-3-methylbenzofuran-2-one having an M.P. of 87–89° after crystallization from petroleum ether.

The 2-(4-cyclohexyl-2-hydroxyphenyl)propionic acid, used as starting material, is produced as follows:

a. 2-(3-cyclohexylphenoxy)propionic acid 11 g of a 55% oily sodium hydride dispersion are deoiled with petroleum ether in an atmosphere of nitrogen, and 500 cc of dry tetrahydrofuran are then added. 44 g of 3-cyclohexyl-phenol in 500 cc of dry tetrahydrofuran are added dropwise within approximately 30 minutes while stirring. 46 g of 2-bromopropionic acid ethyl ester are then added dropwise while stirring. The reaction mixture is heated to 60° for 1 hour and is then allowed to stand at room temperature for 16 hours. The reaction mixture is concentrated by evaporation and the residue is divided thrice between methylene chloride and water. The aqueous phases are again extracted twice with methylene chloride. The organic phases are combined, dried over anhydrous sodium sulphate and concentrated. The residue is boiled at reflux for 2 hours in a solution of 50 g of potassium hydroxide in 900 cc of methanol and 100 cc of water. The reaction solution is concentrated to a great extent by evaporation, acidified to pH = 2 with 2 N hydrochloric acid and extracted thrice with methylene chloride. The organic phases are washed once with water, combined, dried over a anhydrous sodium sulphate and concentrated. Recrystallization of the residue from petroleum ether yields 2-(3-cyclohexyl-phenoxy)propionic acid having an M.P. of 81°–82°.

b. 2-(4-cyclohexyl-2-hydroxyphenyl)propionic acid 2 g of 2-(3-cyclohexyl-phenoxy)propionic acid in 180 cc of 95% ethanol are irradiated with a 150 Watt mercury high pressure burner for 2 hours in an atmosphere of argon and while cooling with water. The solution is concentrated by evaporation and the residue is chromatographed on 150 g of silica gel. By-products are first eluted with ethyl acetate/hexane (1:1). Elution with ethyl acetate finally yields pure 2-(4-cyclohexyl-2-hydroxyphenyl)propionic acid.

NMR spectrum (CDCl$_3$): inter alia δ 1.50 d(J=7 Hz); approximately 2.4 m; 3.92 dd (J = 7 Hz); 6.6–7.2 m; approximately 8.2 m.

The compounds of formula I, including the disclaimed compound, wherein $R_1$ is methyl and $R_2$ is hydrogen and compounds of formula II, excluding the disclaimed compound, exhibit pharmacological activity. In particular, they exhibit anti-inflammatory and edema-inhibiting activity as indicated in standard tests with animals, for example the carrageen edema test in rats.

The compounds are therefore indicated for use as anti-inflammatory and edema-inhibiting agents.

Additionally the compounds exhibit anti-pyretic activity as indicated in standard tests, e.g. the yeast fever test in rats.

The compounds are therefore, further indicated for use as anti-pyretic agents.

Additionally the compounds exhibit analgesic activity as indicated in standard tests, e.g. the phenyl benzoquinone test.

The compounds additionally exhibit platelet aggregation inhibition activity, as indicated by standard tests, e.g. in vitro tests.

The compounds are therefore further indicated for use as blood platelet aggregation inhibitors.

The compounds of formula I, the disclaimed compound of formula I having $R_1$ methyl and $R_2$ hydrogen, and compounds of formula II hereinafter referred to as the "said" compounds, are useful because they possess pharmacological activity in animals. In particular, the said compounds are useful as anti-inflammatory and edema-inhibiting agents, as indicated by standard tests, e.g. the carrageen edema test in rats on p.o. administration of from about 20 to about 60 mg/kg animal body weight of the said compounds.

Additionally the said compounds are useful antipyretic agents for the treatment of fevers, as indicated in standard tests, e.g. the yeast fever test in rats on s.c. administration of from about 30 to about 100 mg/kg animal body weight of the said compounds.

Additionally the said compounds are useful as analgesic agents for the treatment of pains, as indicated in standard tests, e.g. in the phenylbenzoquinone writhing test in mice on p.o. administration of from about 20 to about 50 mg/kg animal body weight of the said compounds.

Additionally the said compuonds are useful as blood platelet aggregation inhibitors, e.g. for the treatment of thrombosis, as indicated in standard tests, e.g. in the collagen in vitro blood platelet test at 5 to 50 μg/ml of the said compounds.

For the above mentioned uses the dosage will, of course, vary depending on the compound employed, mode of administration and therapy desired. However, in general, satisfactory results are obtained when administered at a daily dosage of from 0.2 mg to about 100 mg per kg animal body weight, conveniently given in divided doses 2 to 4 times a day or in sustained release form. For the larger mammal, the total daily dosage is in the range from about 20 to about 1000 and dosage forms suitable for oral administration comprise from about 5 mg to about 500 mg of the compounds admixed with a solid or liquid pharmaceutical carrier or diluent.

The compounds of formula II may be administered in pharmaceutically acceptable salt form. Such salt forms exhibit the same order of activity as the free acid forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts. Such compositions conveniently contain more than 1% by weight of the said compound and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

In a group of compounds $R_2$ in hydrogen. In another group of compounds $R_2$ is methyl. In a sub-group $R_1$ is alkyl or cycloalkyl. In another sub-group $R_1$ is phenyl.

The Example 6 and more especially the Example 1 compound of formula I have particularly interesting activity.

We claim:
1. A compound of formula I,

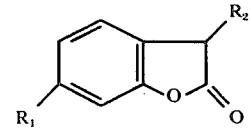

wherein
$R_1$ is cycloalkyl of 3 to 8 carbon atoms or phenyl, and
$R_2$ is hydrogen or alkyl of 1 to 4 carbon atoms.
2. A compound of claim 1 wherein $R_2$ is hydrogen.
3. A compound of claim 1, wherein $R_2$ is methyl.
4. A compound of claim 2 wherein $R_1$ is cycloalkyl.
5. A compound of claim 2 wherein $R_1$ is phenyl.
6. The compound of claim 1 which is 6-cyclohexyl-2,3-dihydro-benzofuran-2-one.
7. The compound of claim 1 which is 6-cyclopentyl-2,3-dihydro-benzofuran-2-one.
8. The compound of claim 1 which is 2,3-dihydro-6-phenyl-benzofuran-2-one.
9. The compound of claim 1 which is 6-cyclohexyl-2,3-dihydro-3-methyl-benzofuran-2-one.

* * * * *